United States Patent [19]

Bazer

[11] Patent Number: 5,063,226
[45] Date of Patent: Nov. 5, 1991

[54] USE OF SUPPLEMENTAL DIETARY RIBOFLAVIN TO INCREASE FERTILITY AND/OR PROLIFICACY IN ANIMALS

[75] Inventor: Fuller W. Bazer, Gainesville, Fla.

[73] Assignee: University of Florida, Gainesville, Fla.

[21] Appl. No.: 503,065

[22] Filed: Mar. 29, 1990

Related U.S. Application Data

[63] Continuation of Ser. No. 220,037, Jul. 15, 1988, abandoned.

[51] Int. Cl.$^5$ .......................................... A61K 31/525
[52] U.S. Cl. .................................................... 514/251
[58] Field of Search ...................................... 514/251

[56] References Cited

PUBLICATIONS

Nutrient Requirements of Domestic Animals, No. 2, 1979 Nutrient Requirements of Swine, 8th Rev. Ed., National Academy of Sciences, National Research Council, Wash., D.C.

Frank, G. R., J. M. Bahr, and R. A. Easter (1984) "Riboflavin Requirements of Gestating Swine", Journal of Animal Science 59:1565-1572.

*Primary Examiner*—Frederick E. Waddell
*Assistant Examiner*—Kimberly Jordan
*Attorney, Agent, or Firm*—Saliwanchik & Saliwanchik

[57] ABSTRACT

A novel method for enhancing the fertility and/or prolificacy of non-ruminant animals is provided. Riboflavin is administered in enhanced levels during gestation and, particularly, during a critical phase of gestation. The beneficial effects are achieved by elevating the concentration of riboflavin in the uterine fluids which surround the developing embryo.

4 Claims, No Drawings

USE OF SUPPLEMENTAL DIETARY RIBOFLAVIN TO INCREASE FERTILITY AND/OR PROLIFICACY IN ANIMALS

This application is a continuation of application Ser. No. 220,037, filed July 15, 1988, now abandoned.

BACKGROUND OF THE INVENTION

Riboflavin, also known as Vitamin $B_2$, is a nutritional factor which occurs naturally in milk, eggs, malted barley, leafy vegetables, yeast, and many other sources. Minute amounts are present in all plant and animal cells. Riboflavin has long been identified as an important component of coenzymes required in the enzymatic oxidation of carbohydrates. Riboflavin has also been found to be a necessary growth factor for the dog and other mammals.

Riboflavin is made by all plants and many microorganisms but not by higher animals. Therefore, it is necessary for higher animals to satisfy riboflavin requirements through dietary intakes. The daily requirements for riboflavin have been established for humans and many agriculturally important animals. For example, the recommended daily allowance for a sedentary 70 kg man has been set by the National Research Council at 1.7 mg.

Dietary allowances have also been established for animals during pregnancy. For example, the currently recommended dietary level of riboflavin in swine feeds is 5.4 mg/day per pregnant pig (Nutrient Requirements of Domestic Animals, No. 2, 1979, Nutrient Requirements of Swine, 8th Revised Edition, National Academy of Sciences, National Research Council, Washington, D.C.). More recently, a dietary intake of 6.4 to 6.6 mg/day for pregnant pigs was recommended (Frank, G. R., J. M. Bahr, and R. A. Easter [1984] Journal of Animal Science 59:1567-1572).

Research leading to the National Research Council recommendations for dietary riboflavin consider the whole of gestation and the amount of dietary riboflavin necessary to allow pigs to have apparently normal pregnancies. However, these recommendations do not take into consideration that the animal's riboflavin requirements during pregnancy can vary during the course of gestation. It is well known that many hormonal and other biochemical changes occur during the course of pregnancy. These changes can trigger different nutritional needs on the part of the mother.

The subject invention provides a method for increasing the success of pregnancy in a variety of animals. The novel method takes into account the unique nutritional requirements of pregnant animals during a specific critical phase of pregnancy.

BRIEF SUMMARY OF THE INVENTION

The current invention concerns providing greatly enhanced quantities of riboflavin during a particular phase of the gestation period of animals. In particular, I have found that there is a specific period of time during gestation when free riboflavin is transported in substantial amounts from maternal blood into the uterine lumen where it becomes a part of the uterine secretions which bathe the embryo. It has also been shown in representative species that this period in gestation is when embryonic mortality is greatest.

By supplying an enhanced level of riboflavin during this critical period of gestation, an increase in fertility and/or prolificacy can be achieved. The novel discovery that riboflavin is transported into the uterine lumen during a specific critical period provides the basis for the method described and claimed here.

DETAILED DESCRIPTION OF THE INVENTION

The subject invention concerns a novel method for increasing fertility and/or prolificacy in animals. In particular, the method involves administering an effective amount of riboflavin, Vitamin $B_2$, to pregnant animals. The method described here may be carried out using any form of free riboflavin, or suitable analogs or derivatives of riboflavin. A suitable analog or derivative would be one which is capable of exerting the same or similar biological effects as riboflavin.

The novel procedures described here can be used to increase fertility and/or prolificacy in any non-ruminant animal. In particular, it is contemplated that this invention can be used to increase fertility and prolificacy in pigs, horses, rodents, rabbits, chickens, turkeys, and mink. Also, the method described here can be used to increase fertility in humans.

The dose of riboflavin, the timing of the treatment, and the method used to administer the treatment will depend upon the type of animal receiving the treatment. For livestock and other non-human animals, the riboflavin may be premixed with feed. Also, the riboflavin may be combined with fructose and corn-soybean meal to create fructose balls which are then ingested by the animal. Intramuscular injections are another means by which the riboflavin may be administered to the animal. These modes of administration are merely illustrative; in general, the riboflavin may be administered in any way which enables the compound to exert its biological effects.

For use in humans, the means by which the riboflavin can be administered include, but are not limited to, oral formulations, intramuscular injections, and intravenous injections.

The administration of riboflavin in accordance with this novel invention occurs to the female after conception. Enhanced levels of riboflavin may be administered throughout the gestation period. However, it is most important that enhanced levels of riboflavin be maintained within the mother during a specific sensitive period during gestation. Specifically, I have discovered that there is a critical period during gestation when free riboflavin is transported in substantial amounts from maternal blood into the uterine lumen where it becomes a part of the uterine secretions which bathe the embryo.

It is known that embryo mortality does not occur at the same rate during the entire period of gestation. There are specific times during gestation when embryo mortality is most likely to occur. In particular, embryo mortality has been shown to be especially high during the same time period when riboflavin is observed in the uterine secretions. Embryo mortality during this critical "gestational riboflavin phase" can account for significant reductions in the pregnancy rates in many animals.

Determination of when this critical gestational riboflavin phase occurs for a particular species is easily accomplished by techniques which are well known in the animal breeding science. These procedures, which are discussed in detail in Bazer et al. (Bazer, F. W., R. M. Roberts, D. C. Sharp III [1978] "Collection and Analysis of Female Genital Tract Secretions," in *Methods in Mammalian Reproduction,* pp. 503-528, Academic Press, New York, N.Y.), involve introducing physiological saline into the uterine lumen and then recovering it.

The presence of riboflavin in uterine flushings can be detected visually by its characteristic yellow color. The presence of riboflavin can also be verified and quantified by electromagnetic absorption measurements at a wavelength of 446 nm. These determinations are well within the skill of a person trained in analytical techniques and animal sciences.

The dosage of riboflavin which is administered to the pregnant animal in accordance with the invention described here is simply that dosage which is sufficient to produce a significant increase in the free riboflavin concentration measured in the uterine flushings. Although it is now recognized that riboflavin is transferred from maternal blood into the uterine lumen, the rate of this transfer and the exact mechanisms by which it is triggered and occurs is not well characterized in all animals. Therefore, it is possible that low dosages of riboflavin may not be sufficient to produce a biologically significant increase in riboflavin concentration in the uterine secretions which bathe the developing embryo during this critical period. Because no toxic effects have been attributed to riboflavin, it is possible to administer greatly enhanced levels of riboflavin without concern about adverse physiological consequences. Therefore, dosages of riboflavin which increase the riboflavin concentration in the uterine secretions by at least 10% are preferred.

The enhanced dosages of riboflavin may be administered throughout gestation but are or primary importance during the period which begins about 2 days before the critical gestational riboflavin phase and continues until about two days after the end of this phase.

Following is an example which illustrates the novel method, including the best mode, of the invention claimed here. This example is illustrative and should not be construed as limiting.

EXAMPLE 1

Enhanced Dietary Riboflavin in Pregnant Swine

Swine diets must include supplemental riboflavin because of an inadequate supply of this vitamin in most plant-derived swine feeds.

It has been observed that uterine flushings of pigs, obtained by introducing physiological saline into the uterine lumen and then recovering it, have a distinct yellow color on days 7 through 9 of the estrous cycle, or pregnancy. This yellow color is due to the presence of free riboflavin which is transported into the uterine lumen in response to decreasing concentrations of estrogens and increasing concentrations of progesterone, characteristic of days 6 through 9 of the estrous cycle and pregnancy (Murray, F. A., R. J. Moffatt and A. P. Grifo, Jr. [1980] Journal of Animal Science 50:926-929; Moffatt, R. J., F. A. Murray, A. P. Grifo, Jr., L. W. Haynes, J. E. Kinder and G. R. Wilson [1980] Biology of Reproduction 23:331-335). In particular, it has been found that riboflavin (Rb) increases in uterine flushings of cyclic and pregnant gilts between days 6 and 8 after onset of estrus and then decreases to undetectable levels by day 11.

It has also been established that pig embryos go through a critical stage of development during the period between days 7 and 10 of gestation, and 25 to 50% of them die during or shortly after this period (see Bazer, F. W. and N. L. First [1983] Journal of Animal Science 57 [Supplement 2]:425-460).

In order to test the effects of enhanced dietary riboflavin on pregnant swine, 8 cyclic gilts received 2.2 kg/day of a corn-soybean meal diet plus either 0 (control) or 100 mg additional riboflavin per day on days 4 through 7. Uterine flushings were collected on day 8 and total riboflavin was quantified by measuring its absorption at 446 nm. It was found that riboflavin was higher ($P=0.06$) in uterine flushings from gilts fed the enhanced levels of riboflavin ($166\pm11$ μg vs. $117\pm21$ μg). Additionally, 14 control and 15 riboflavin-fed gilts were mated, received either 0 or 100 mg riboflavin on days 4 through 10 and were hysterectomized on day 30.

From these experiments it was found that live embryos ($11.5\pm0.8$ vs. $13.2\pm0.5$, $P=0.07$), embryonic survival (75% vs. 84%, $P<0.05$) and allantoic fluid volumes ($200\pm7$ ml vs. $235\pm5$ ml, $P<0.05$) were greater for the gilts which had been fed riboflavin than for the controls. Also, 48 control and 51 riboflavin-fed primiparous sows were fed 2.3 kg/day of a corn-soybean meal ration plus either 0 or 100 mg of riboflavin on days 4 through 10 and allowed to farrow. Farrowing rate was higher ($P<0.05$) for the riboflavin-fed sows (80.4%) than for the control (70.8%) sows.

It was also found that sows which had been fed the enhanced levels of riboflavin had the following reproductive advantages: total piglets born, $8.2\pm0.5$ vs. $9.3\pm0.5$, $P<11$; piglets born alive $7.8\pm0.5$ vs. $9.0\pm0.5$, $P<0.09$; piglets alive at day 21, $6.8\pm0.4$ vs. $8.4\pm0.4$, $P<0.01$; piglets alive at day 42, $6.7\pm0.4$ vs. $8.3\pm0.4$, $P<0.01$; total litter weight at day 21, $35.0\pm2.1$ kg vs. $41.6\pm1.9$ kg, $P<0.02$; and total litter weight at day 42, $72.2\pm4.3$ g vs. $86.7\pm3.9$ kg, $P<0.01$.

These results, which are summarized in Tables 1 through 4, indicate that 1) riboflavin in uterine flushings of pigs can be increased by feeding 100 mg supplemental of riboflavin on days 4 through 8 of the estrous cycle; 2) supplemental dietary riboflavin is associated with higher litter size, embryonic survival, and allantoic fluid volume at day 30 of gestation; and 3) riboflavin treated sows had higher rates of conception, more live piglets at birth, at days 21 and 42, and greater total litter weights at days 21 and 42 of lactation.

TABLE 1

Effect of supplemental dietary riboflavin, 100 mg/day, on days 4 through 7 on total recoverable riboflavin in uterine flushings on day 8, $X \pm$ SEM

| Item | Treatment Groups | |
|---|---|---|
| | Control | Riboflavin |
| Gilts, No. | 4 | 4 |
| Total Riboflavin, μg | $117 \pm 21$ | $166 \pm 21$* |

*$P = .06$, 42 percent increase

TABLE 2

Effect of supplemental dietary riboflavin, 100 mg/day, on days 4 through 10 on reproductive performance of gilts at day 30 of gestation, $X =$ SEM

| Item | Treatment Groups | |
|---|---|---|
| | Control | Riboflavin |
| Gilts pregnant, No. | 10/14 | 13/15 |
| Pregnancy rate, % | 71.4 | 86.6 |
| Corpora lutea, No. | $14.7 \pm .4$ | $15.6 \pm .7$ |
| Embryos, No. | | |
| Total | $12.4 \pm .5$ | $14.0 \pm 6^a$ |
| Live | $11.5 \pm .8$ | $13.2 \pm 5^b$ |
| Weight, g | $1.9 \pm .1$ | $1.8 \pm .1$ |
| Embryonic Survival, % | 78.2 | 84.2* |

TABLE 2-continued

Effect of supplemental dietary riboflavin, 100 mg/day, on days 4 through 10 on reproductive performance of gilts at day 30 of gestation, X ± SEM

| Item | Treatment Groups | |
|---|---|---|
| | Control | Riboflavin |
| Placental weight, g | 34 ± 1 | 36 ± 1 |
| Allantoic fluid, ml | 200 ± 7 | 135 ± 5** |

$^a$P < .1
$^b$P < .07
*P < .05
**P < .01

TABLE 3

Effect of supplemental dietary riboflavin, 100 mg/day, on days 4 through 10 of pregnancy in reproductive performance of sows at farrowing, X ± SEM

| Item | Treatment Groups | |
|---|---|---|
| | Control | Riboflavin |
| Sows pregnant, No. | 34/48 | 41/51 |
| Pregnancy rate, % | 70.8 | 80.4* |
| Litter size, No. | | |
| Total | 8.2 ± .5 | 9.3 ± .5$^a$ |
| Live | 7.8 ± .5 | 9.0 ± .5$^b$ |
| Dead | .4 ± .1 | .3 ± .1 |
| Litter weight, kg | | |
| Total | 12.5 ± .7 | 13.6 ± .6 |
| Individuals | 1.6 ± .1 | 1.6 ± .1 |

*P < .05
$^a$P < .11
$^b$P < .09

TABLE 4

Effect of supplementary dietary riboflavin, 100 mg/day, on days 4 through 10 of gestation and litter performance during lactation, X ± SEM

| Item | Treatment Groups | |
|---|---|---|
| | Control | Riboflavin |
| Litter Size, No. | | |
| Birth | 7.8 ± .5 | 9.0 ± .5 |
| Day 21 | 6.8 ± .4 | 8.4 ± .4** |
| Day 42 | 6.7 ± .4 | 8.3 ± .4** |
| Total litter wt., kg | | |
| Birth | 12.5 ± .7 | 13.6 ± .6 |
| Day 21 | 35.0 ± 2.1 | 41.6 ± 1.9* |
| Day 42 | 72.2 ± 4.3 | 86.7 ± 3.9** |
| Piglet weights, kg | | |
| Birth | 1.6 ± .1 | 1.6 ± .1 |
| Day 21 | 5.1 ± .4 | 5.1 ± .2 |

TABLE 4-continued

Effect of supplementary dietary riboflavin, 100 mg/day, on days 4 through 10 of gestation and litter performance during lactation, X ± SEM

| Item | Treatment Groups | |
|---|---|---|
| | Control | Riboflavin |
| Day 42 | 10.9 ± .4 | 10.7 ± .4 |

*P < .05
**P < .01

From the results presented in Tables 1 through 4, it can be seen that the advantage of the use of supplementary dietary riboflavin at 100 mg/day on days 4 through 10 is that it allows a significant increase in free riboflavin in uterine secretions and is associated with a significant increase in the percentage of sows that become pregnant and the size of the litters that they produce. Increased fertility and prolificacy of pigs are the primary determinants of reproductive efficiency. This invention increases the level of both in pregnant swine.

In summary, the following advantages to reproductive performance resulted from feeding 100 mg/day on days 4 through 10 of pregnancy:

1. Percentage of pigs mated that became pregnant was 10–15% higher.
2. Percentage of embryos surviving and litter size at day 30 of pregnancy were significantly higher.
3. Allantoic fluid volumes at day 30, indicative of placental development, were greater.
4. Piglets born alive, piglets alive at day 21 of lactation, and piglets weaned at day 42 of lactation were greater as was total litter weight weaned.

I claim:

1. A method for increasing the pregnancy rate and litter size in swine, said method comprising the administration of enhanced levels of riboflavin to a swine during a period which commences on about day 4 of the gestation period of said swine and ends on about day 10 of said gestation period; wherein the dosage of said riboflavin is at least about 100 mg/day and is sufficient to increase the concentration of riboflavin in uterine secretions of said swine by at least about 10%.

2. The method, according to claim 1, wherein the amount of riboflavin in said swine's uterine secretions is increased to at least about 166 μg.

3. The method, according to claim 1, wherein said enhanced levels of riboflavin are administered to said swine from about day 4 to about day 7 of said swine's gestation period.

4. The method, according to claim 1, wherein said administration of enhanced levels of riboflavin is accomplished by means selected from the group consisting of pre-mixed feed, fructose formulations, intramuscular injections, and intravenous injections.

* * * * *